(12) United States Patent
Liska et al.

(10) Patent No.: US 9,199,062 B2
(45) Date of Patent: Dec. 1, 2015

(54) INSERTER ASSEMBLY FOR A PERIPHERAL CATHETER WITH A PLASTER MEMBER, METHOD OF CONFIGURING THE INSERTER ASSEMBLY WITH THE PERIPHERAL CATHETER, AND METHOD OF PERFORMING A BLOOD VESSEL PUNCTURE

(75) Inventors: Jan Liska, Stockholm (SE); Madelene Eklund, Uppsala (SE); Dan Karlsson, Jönköping (SE); Jimmy Gidö Schon, Jönköping (SE); Johan Rinman, Jönköping (SE)

(73) Assignee: Tradinco AB, Stockholm (SE)

( * ) Notice: Subject to any disclaimer, the term of this patent is extended or adjusted under 35 U.S.C. 154(b) by 1112 days.

(21) Appl. No.: 13/256,888

(22) PCT Filed: Mar. 10, 2010

(86) PCT No.: PCT/EP2010/053039
§ 371 (c)(1),
(2), (4) Date: Sep. 15, 2011

(87) PCT Pub. No.: WO2010/105954
PCT Pub. Date: Sep. 23, 2010

(65) Prior Publication Data
US 2012/0010577 A1    Jan. 12, 2012

(30) Foreign Application Priority Data

Mar. 20, 2009  (EP) ..................................... 91557678

(51) Int. Cl.
*A61M 25/00* (2006.01)
*A61M 25/06* (2006.01)
*A61M 25/02* (2006.01)
(52) U.S. Cl.
CPC ....... *A61M 25/0606* (2013.01); *A61M 25/0097* (2013.01); *A61M 25/02* (2013.01); *A61M 25/0612* (2013.01); *A61M 2025/0266* (2013.01)

(58) Field of Classification Search
CPC ............ A61M 25/0097; A61M 25/02; A61M 2025/0266; A61M 25/0606; A61M 25/0612
USPC ............. 604/164.01, 164.04, 164.08, 164.11, 604/164.12, 165.03
See application file for complete search history.

(56) References Cited

U.S. PATENT DOCUMENTS 3,856,020 A * 12/1974 Kovac ....................... 604/170.03
7,083,598 B2    8/2006 Liska ............................ 604/180
(Continued)

FOREIGN PATENT DOCUMENTS

EP          2 022 421 A1    2/2009
WO    WO 2009/016184 A1    2/2009

OTHER PUBLICATIONS

International Search Report & Written Opinion, PCT/EP2010/053039, mailed Jun. 7, 2010.
(Continued)

*Primary Examiner* — Emily Schmidt
*Assistant Examiner* — Lauren M Peng
(74) *Attorney, Agent, or Firm* — Winston & Strawn LLP

(57) ABSTRACT

An inserter assembly for a peripheral catheter assembly configured with an adhesive plaster member, wherein the catheter tube extends through the plaster member. The inserter assembly includes a first inserter part having first and second legs, a bridge member connecting the first and second legs at a distance from each other, with the bridge member adapted for detachably engaging or holding at least a part of the needle module extending coaxially between the first and second legs. The inserter assembly includes a second inserter part for covering the needle. The plaster member impairs visual sight and the line of vision to the needle tip during puncture may be impaired. To prevent this the first inserter part serves for holding a back-folded part of the plaster member.

20 Claims, 9 Drawing Sheets

(56) References Cited

U.S. PATENT DOCUMENTS

| | | | |
|---|---|---|---|
| 2001/0039401 A1 | 11/2001 | Ferguson et al. | 604/198 |
| 2004/0044314 A1 | 3/2004 | Liska | 604/180 |
| 2006/0041231 A1* | 2/2006 | Pressly et al. | 604/164.08 |
| 2007/0049868 A1* | 3/2007 | Woehr et al. | 604/110 |
| 2009/0036836 A1 | 2/2009 | Nystrom et al. | 604/180 |

OTHER PUBLICATIONS

Partial European Search Report, EP 09 15 5767, mailed Jun. 24, 2009.

* cited by examiner

INSERTER ASSEMBLY FOR A PERIPHERAL CATHETER WITH A PLASTER MEMBER, METHOD OF CONFIGURING THE INSERTER ASSEMBLY WITH THE PERIPHERAL CATHETER, AND METHOD OF PERFORMING A BLOOD VESSEL PUNCTURE

This application is a 371 filing of International Patent Application PCT/EP2010/053039 filed Mar. 10,2010.

BACKGROUND

The present invention relates to an inserter assembly for a peripheral catheter assembly of the kind comprising a hollow catheter hub having a female proximal end and a distal end provided with a catheter tube, a needle module having a male coupling part for engaging the female proximal end of the hollow catheter hub and provided with a needle extending inside the catheter tube and having a pointed tip protruding from the catheter tube, and a plaster member having a first adhesive surface and an opposing second surface, wherein the catheter tube extends through the plaster member from the first surface to the second surface.

The invention further relates to a method for configuring a peripheral catheter integral with a plaster member with the inserter assembly and a method for performing a venipuncture using the same.

It is often necessary to insert a flexible catheter tube into a vein and leave the catheter tube inside the vein for example for administering intravenous fluids or taking blood samples thereby avoiding repeated venipunctures. A hollow needle carrying the catheter tube and having a pointed tip protruding from the catheter tube is used to make a venipuncture and insert the catheter tube. Subsequently the needle is retracted and disposed of and the needle is secured by means of plaster strips to avoid dislocation.

Within the recent years a new kind of peripheral catheters has come to light that keep the injection site isolated from its surroundings to reduce risk of infection. The applicant's U.S. patent application U.S. Pat. No. 7,083,598 discloses such a peripheral catheter with an integrated plaster member for adhering to the skin area around the puncture site once the catheter has been inserted into the vein. A variant of the peripheral catheter is disclosed in the applicant's International Patent Application PCT/EP2008/059950.

While the advantage of the integrated plaster member is that the plaster member protects the puncture site from getting into contact with the surroundings, including the fingers of the operator making the puncture, the plaster member impairs visual sight. In particular the line of vision to the needle tip during puncture may be impaired. The freely flapping plaster member further complicates manipulation of the integral structure during puncture.

SUMMARY OF THE INVENTION

It is a main aspect of the present invention to provide an inserter assembly for providing a free line of vision during puncture using a peripheral catheter having an integrated plaster member.

It is a second aspect of the present invention to provide an inserter assembly for providing a controlled insertion of a peripheral catheter having an integrated plaster member.

It is a third aspect of the present invention to provide an inserter assembly which can be detached from a peripheral catheter of the kind having an integrated plaster member subsequent to insertion of a catheter tube without discomfort to the client.

It is a fourth aspect of the present invention to provide an inserter assembly of the kind mentioned in the opening paragraph which is easy and inexpensive to fabricate.

It is a fifth aspect of the present invention to provide an inserter assembly of the kind mentioned in the opening paragraph which safeguards a person handling the combined inserter assembly and peripheral catheter from accidental needle pricks at any stage of manipulation.

The novel and unique whereby this is achieved according to the present invention consists in that the inserter assembly comprises a first inserter part having a first leg and a second leg, a bridge member connecting the first leg and the second leg at a distance from each other, which bridge member is adapted for detachably engaging or holding at least a part of the needle module extending coaxially between said first leg and said second leg.

Because both the first leg and the second leg extend along the length of the needle module, the catheter hub can be secured to the bridge member to facilitate a controlled and guided insertion of the needle in a blood vessel of a patient. The bridge member provides a sufficient gap between the first leg and the second leg to hold the needle module in an operable manner during both insertion of the over-the-needle catheter tube, and when used for retracting the needle to leave the catheter tube inside the blood vessel. Thus, the first inserter assembly part improves controllability and maneuverability during all stages of insertion of the peripheral catheter and complications, such as hematomas resulting from failure to puncture a vein when the needle is inserted or when the needle is removed, can be kept at a minimum.

The bridge member may have a means for holding and/or engaging a part of the needle module. For example the bridge member may have a protruding hollow male part for firmly engaging the female proximal end of the catheter hub, to facilitate a very easy retraction of the needle from the catheter tube after appropriate insertion of the catheter tube. In this case the bridge member is part of the needle module. Alternatively, the bridge member can have a protruding clamp or have a recess for securing the bridge member to the female proximal end of the catheter hub, for example by snap fitting or force fitting, in which case the bridge member is a separate part. It should be noted that although the term "first inserter part" is used, this term should not be construed as limiting the functionality of this component, which also is used to e.g. retract the needle and hold the plaster member, as will be more clearly understood when reading the following description and studying the drawing.

Retraction of the needle is simply made by moving the first inserter part with the needle module engaging or hold by the bridge member away from the puncture site, thereby disengaging the male coupling part of the needle module from the female proximal end of the catheter hub.

In a preferred embodiment the first leg and the second leg have respective proximal ends and opposing distal ends, and the bridge member connects the first leg and the second leg a distance from the respective proximal ends thereby configuring the first inserter part substantially as an H-shaped holder for the needle module. The bridge member constitutes the crossbar of the substantially H-shaped first inserter part and delimits together with the first leg and the second leg opposing proximal and distal spaces for accommodating a lengthwise section of the needle module.

Although preferred, the bridge member needs not connect to the first leg and the second leg at right angles at the centre point of a leg but can be connected anywhere at any angle between the proximal end and the distal end of said legs.

In a preferred embodiment the distance between the proximal end of a leg and the bridge member's corresponding connecting point on a leg is shorter than the distance between said connection point and the distal end of said leg. In this embodiment the H-shaped first inserter part has a proximal space facing the proximal ends of the legs. The distal space opposite the proximal space accommodates at least the catheter hub and the major part of the catheter tube, as well as a male coupling part of the bridge member may protrude in said proximal space for engaging the catheter hub.

To provide a clear line of vision to the puncture site the first leg and the second leg may be provided with a means for detachably holding a back-folded part of the plaster member as long as required.

Such means for detachably holding a back-folded part of the plaster member serves for preventing the plaster member from self-straightening during puncture, and can for example be a hook or a U-bend extension provided at the distal end of each respective leg. The legs may be inherent flexible in relation to each other, at least just a little, due to the nature of the selected manufacturing materials or due to structural design, to enable the distal ends of the opposing first and second legs to move apart along a folding line of the back-folded plaster member, for example when exterior force is applied to the proximal ends of the legs, to thereby set the plaster member free. Plastic polymeric materials are suitable materials for manufacturing the first inserter part. The hook or U-bend extension can advantageously be made integral with a leg in a moulding process.

When the proximal ends of the first leg and the second leg have enlarged finger grip sections application of force can be made very easy, and the risk that the operator looses the grip at the first inserter part during operating the peripheral catheter assembly, is substantially reduced. The finger grip sections can be provided with an uneven surface, e.g. being serrated, corrugated or embossed or have a frictional coating, to further ensure a firm grip at the first inserter part.

The flexibility of the legs of the first inserter part can advantageously by achieved if the connection between the first leg and a first end of the bridge member is configured to function as a first pivot, and the connection between the second leg and the second end of the bridge member opposite the first end is configured to function as a second pivot, preferably so that the first leg and the second leg can be pivoted to and from each other along the length of the needle module.

Due to the legs ability to pivot at least slightly about the connection points to the bridge member, which connection points serve as pivots, the legs can advantageously be forced towards each other simply by means of the fingers, if for example extra clamping force for holding the needle module between the first leg and the second leg is required. The first pivot and the second pivot may thus serve as fulcrums for the first leg and the second leg, respectively.

Depending on the location of the bridge member the pivots may be configured to arrange the first leg and the second leg as a lever allowing the first leg and the second leg to flex in relation to each other upon application of an exterior force on a leg. The size of the exterior force required for spreading and bringing together the first leg and the second leg depends on several factors, including but not limited to the type of lever, the length of the legs and of the bridge member, and the material of which the components of the inserter assembly is fabricated.

Within the scope of the present invention the preferred lever arrangement is a first class lever arrangement, i.e. the lever is understood as a bar, in this case a leg, pivotable arranged on a pivot, i.e. the fulcrum, located offset from the free ends of the leg to define opposing lever arms. When exterior force is applied to an arm, e.g. by depressing the free end of the leg, the other arm swings about the pivot. The first inserter part may in the alternative be configured with second class lever legs which have opposing pivots located at the ends of the legs opposite free ends of the legs to define two opposing single lever arms, where exterior force is applied at the free end of the arms. In yet an alternative embodiment the first inserter part may be configured with third class lever legs, which have opposing pivots located at the end of the legs and application of force is made on the legs between the pivots and the free ends of the legs.

In the most preferred embodiment the inserter assembly further comprises a second inserter part including a needle cover part to improve operator safety.

The second inserter part may have a first clamping arm and a second clamping arm attached to the needle cover part, which first clamping arm and second clamping arm may be adapted for detachably coupling with the first inserter part's means for detachably holding a back-folded part of the plaster member. Thus the second inserter part not only serves for preventing accidental needle pricks, it also assists in holding the back-folded plaster member in the back-folded position when the first inserter part engages the needle module.

Detachable coupling together of the first inserter part and the second inserter part can easily be achieved if the first clamping arm has a free end provided with a first clamp means and the second clamping arm has a free end provided with a second clamp means.

Coupling and decoupling of the first and second inserter part can for example be made if the first clamping arm and the second clamping arm are resiliently arranged on the needle cover part. The resilient arrangement facilitates a careful decoupling of the second inserter part from the first inserter part, and ensures that the back-folded plaster member remains in its back-folded position held by the first inserter part during decoupling. Thus the second inserter part can just be "clicked" or snap-fitted on the first inserter part.

The peripheral catheter described above is configured with the inserter assembly according to the present in a method comprising the steps of
  mounting the needle module in or at the bridge member of the first inserter part,
  folding the plaster member back towards the proximal end of the first leg and the second leg of the first inserter part,
  mounting the second inserter part to cover the needle of the needle module, and
  coupling the first inserter part and the second inserter part together.

The peripheral catheter described above is used together with the inserter assembly according to the present invention in a method for performing a blood vessel puncture, which method comprises the steps of
  detaching the second inserter part from the first inserter part,
  optionally pressing the first leg and second leg of the first inserter part together towards the needle module,
  inserting the catheter tube in the blood vessel,
  retracting the needle by retracting the first inserter part thereby leaving the catheter tube inside the blood vessel and setting the plaster member free, and
  adhering the plaster member to a skin surface around the puncture site.

BRIEF DESCRIPTION OF THE DRAWINGS

The invention will now be described with reference to the drawing in which.

DETAILED DESCRIPTION OF THE INVENTION

Figure 1:
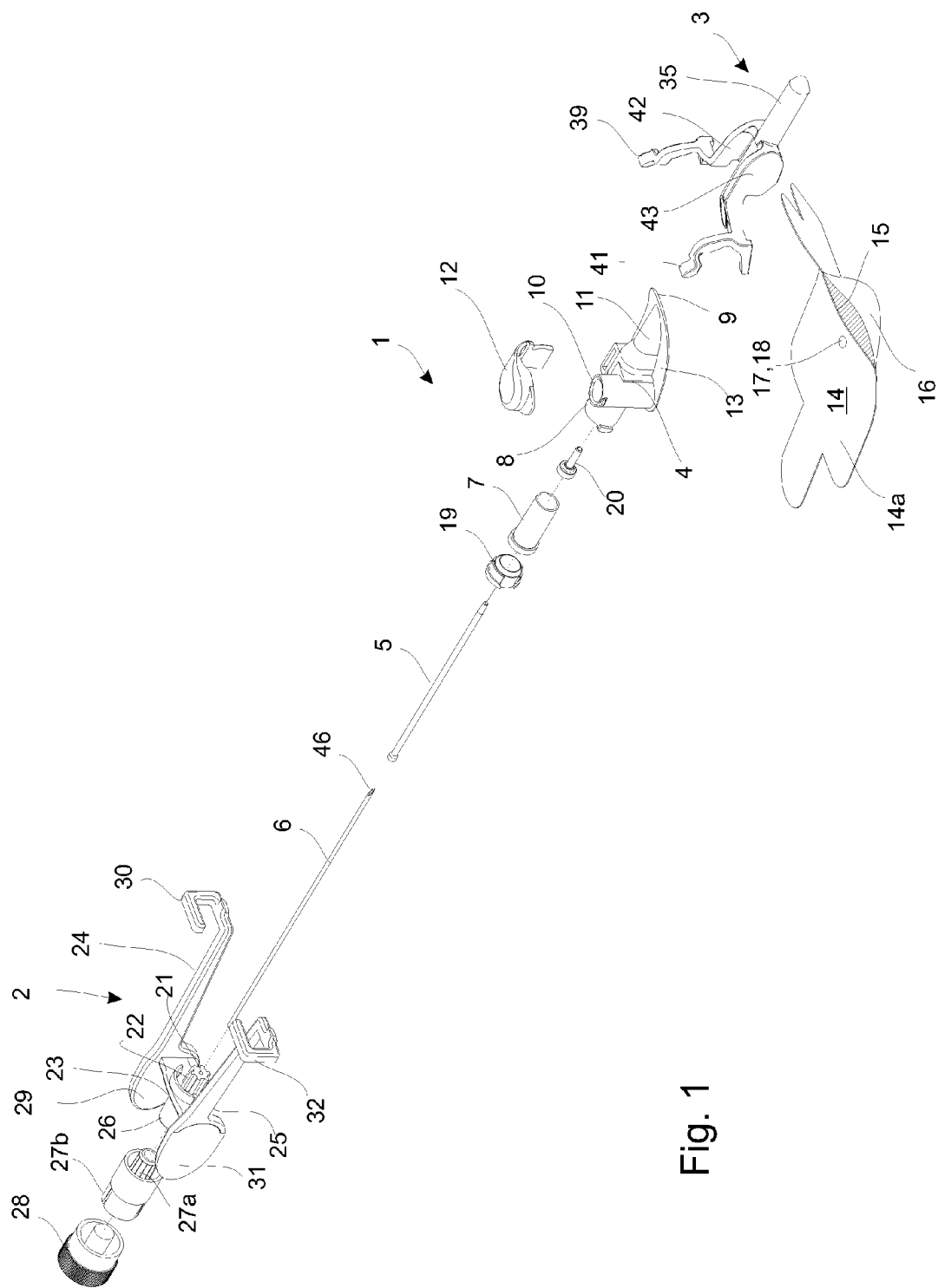
FIG. 1 shows, seen in perspective, an exploded view of the peripheral catheter and the inserter assembly.

In the perspective exploded view of FIG. 1 the components for a peripheral catheter 1 are shown together with a first inserter assembly part 2 and a second inserter assembly part 3. The peripheral catheter assembly, which is designated in its entirety with the reference numeral 1, consists of a hollow catheter hub 4, a flexible over-the-needle catheter tube 5, a needle 6 and a valve sealing 7, which fits into the catheter hub 4 so seal the hub 4 from blood spillage after venipuncture. The hollow catheter hub 4 has a female proximal end 8 for receiving a complementarily shaped male part and a distal end 9. An infusion port 10, a "chimney", merges perpendicularly into the hollow catheter hub 4 to allow fluid communication between the bore 11 of the hollow catheter hub 4 and the infusion port 10. Other angular relationships are intended within the scope of the present invention. The infusion port 10 has a pivotable flap lid 12, but closure means such as membranes or plugs are suitable alternatives. An attachment member 13 protrudes from the catheter hub 4 to provide an enlarged, flat attachment area and surface for the catheter hub 4 when the peripheral catheter assembly 1 is secured to the patients skin subsequent to insertion in a vein. The attachment member 13 is combined with the catheter hub 4, e.g. using adhesive substances, in particular glue, or is moulded together with the catheter hub 4 in one single process, such as e.g. injection moulding. The attachment member 13 is united with a plaster member 14 for adhering the peripheral catheter assembly 1 to a subjacent skin surface (not shown). The plaster member 14 is provided with an adhesive 15, which is protected by a releasable cover sheet 16. The plaster member 14 and the cover sheet 16 have superposing traversing apertures 17,18, respectively, for allowing the catheter tube 5 and the needle 6 to pass through when a venipuncture is made.

The valve sealing 7 fits intimately into a bore 11 of the catheter hub 4 between the female proximal end 8 and the distal end 9 and is, in the case shown, arranged between an annular locking ring 19 at the female proximal end 8 and a connection piece 20 for the catheter tube 5 at the distal end 9 of the catheter hub 4.

The peripheral catheter assembly, including catheter hub 4 and sealing valve 7 for use with the inerter assembly 2,3 according to the present invention may be of known kind, for example the peripheral catheter assembly as disclosed in the applicants International patent application PCT/EP2008/059950.

An obturator module for the over-the-needle catheter tube 5 consists of the hollow needle 5, which is secured in a bore 21 of a knurled male socket 22 protruding from a bridge member 23 between the first inserter part 2's opposing first leg 24 and second leg 25. The hollow needle 5 provides for fluid communication between the vein and the exterior environment when fully inserted into a vein. The bore 21 of the male socket 22 opens into a female plug 26, optionally a tapering female plug 26, which a complementary shaped connector 27, e.g. a Luer connector, for attachment of a drip. The female plug 26 can also be closed with a suitable closure means, such as a removable plug 28, a permanent closure or combination of these, either directly or via the connector 27.

Although knurled exterior surfaces are shown in the figures on male sockets, couplings or exterior grips, other kinds of surfaces may also be implemented for providing reliable and secure engagement or finger gripping capability.

Figure 2:
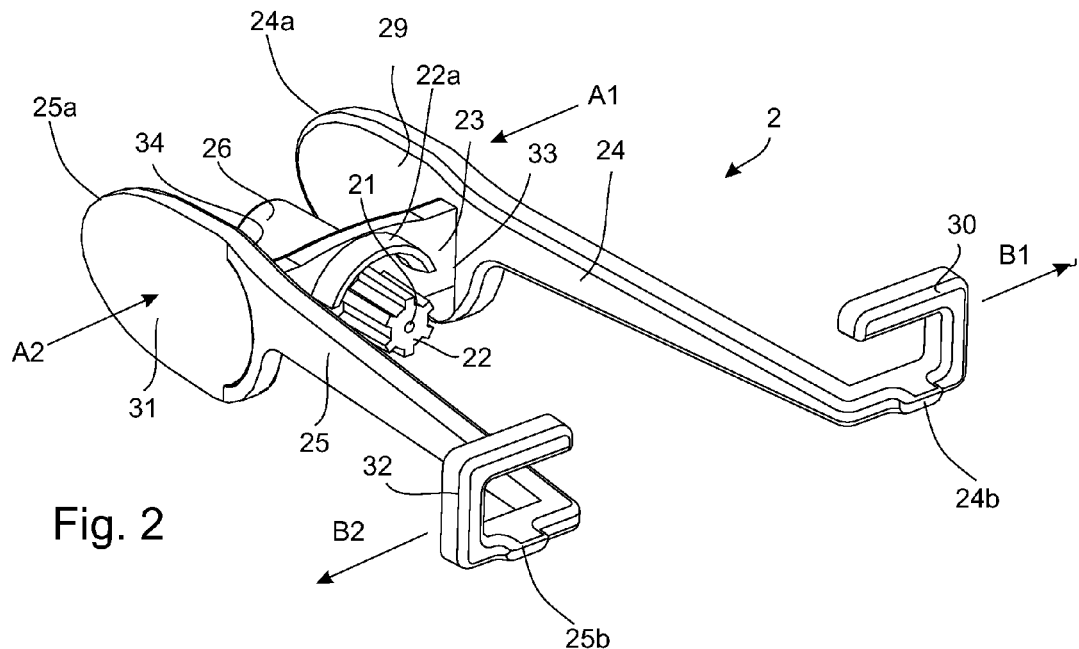
FIG. 2 shows, seen in perspective, the first inserter part seen from the distal end.
Figure 3:
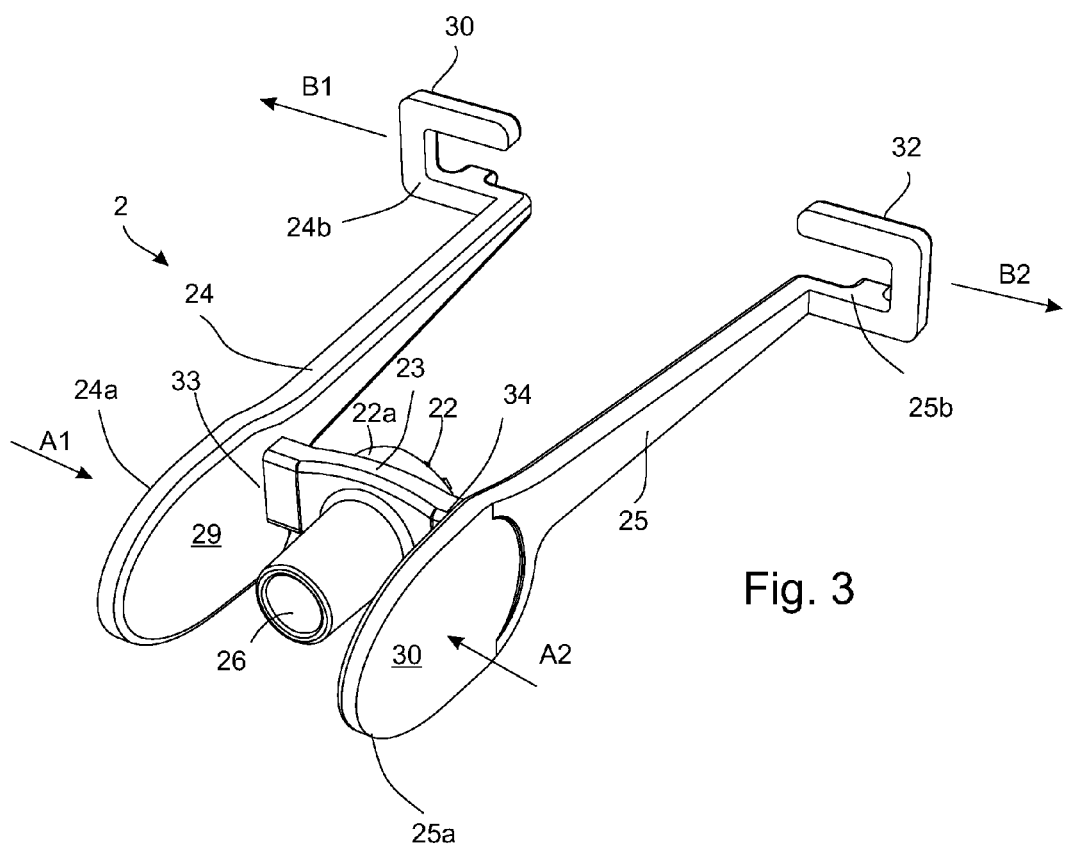
FIG. 3 shows the same seen from the proximal end.

The first inserter part 2 is seen in perspective from the distal end in the enlarged scale view in FIG. 2 and from the proximal end in the enlarged scale view of FIG. 3. The first inserter part 2 has a first leg 24 with a proximal end 24a configured as a flat finger grip plate 29, and an opposing distal end 24b configured as an U-shaped bending 30 extending perpendicular to the first leg 24 at the distal end of said first leg 24. Correspondingly, the second leg 25 has a proximal end 25a configured as a flat finger grip plate 31 and an opposing distal end 25b configured as an U-shaped bending 32 extending perpendicular to the second leg 25 at the distal end of said second leg 25. The openings of the U-bendings 30,32 face against each other. The first leg 24 is interconnected with the second leg 25 by means of bridge member 23, in this case a bar 23, attached at a first connection point 33 to the first leg 24 and serving as a first pivot 33, and attached at a second connection point 34 to the first leg 25 and serving as a second pivot 34 when force are applied to the flat finger grip plates 29,31 in the directions indicated with the arrows A1,A2 towards each other, thereby forcing the opposing U-shaped bendings 30,32 away from each other as indicated with the arrows B1,B2. Thus, the first inserter part 2 is configured substantially as an H, where the crossbar of the H allows both opposing legs 24,25 to flex to and from each other upon application on external force. As is seen both in FIGS. 2 and 3 the male knurled socket 22 extends from the bar 23 of the bridge member 23 between the first leg 24 and the second leg 25 towards the respective distal ends 24b,25b, and the female plug 26 extends axially opposite between the first leg 24 and the second leg 25 towards respective proximal ends 24a,25a, thereby configuring the bridge member 23 as a cross. An arched backstop or pressure plate 22a aids in holding the catheter hub 4 securely secured to the first inserter part 2.

Figure 4:
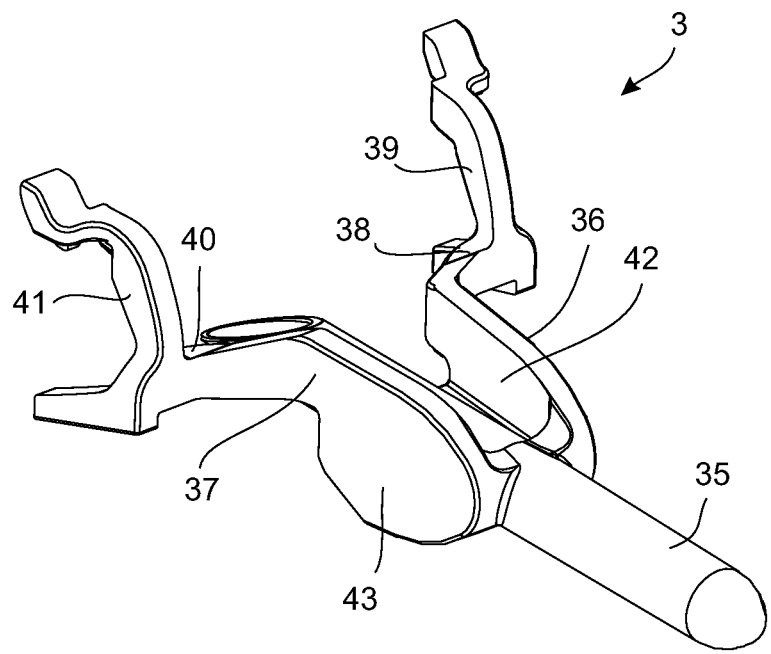
FIG. 4 shows, seen in perspective, the second inserter part seen from the distal end.
Figure 5:
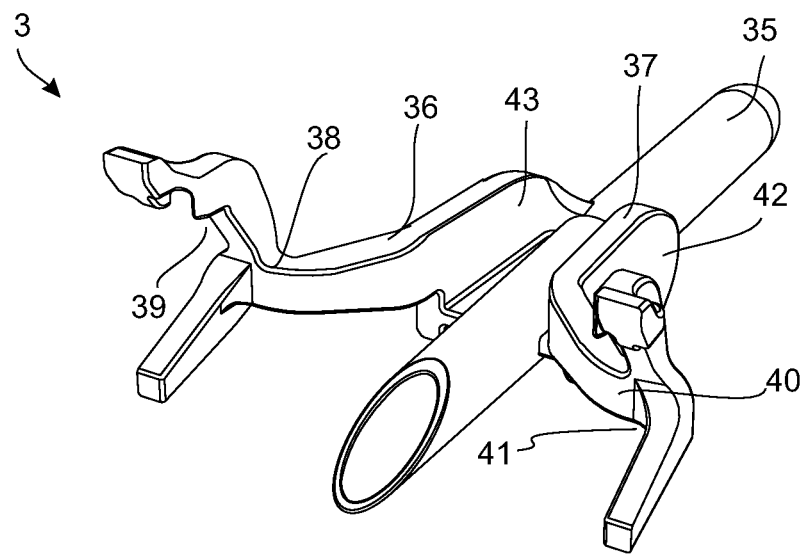
FIG. 5 shows the same seen from the proximal end.

The second inserter part 2 is seen in perspective from the distal end in the enlarged scale view in FIG. 4 and from the proximal end in the enlarged scale view of FIG. 5. The second inserter part 3 has a hollow tubular needle cover part 35, a first clamping arm 36 and an opposing second clamping arm 37 secured to the needle cover part 35. The first clamping arm 36 has a free end 38 provided with a clamp means 39 configured as a flexible first claw 39, and the second clamping arm 37 has a free end 40 provided with a clamp means 41 configured as a flexible second claw 41. The first clamping arm 36 and the second clamping arm 37 are secured to the needle cover part 35 at finger grip ends configured as enlarged plates 42,43 opposite the respective free ends 38,40, optionally to enable the clamping arms 36,37 to flex towards the longitudinal axis of the needle cover part 35. The first claw 39 and the second claw 41 are designed for detachably coupling with the U-bendings 30,32 of the first leg 24 and the second leg 25, respectively, of the first inserter part 2 as will be described in more detail with reference to the additional figures.

Figure 6:
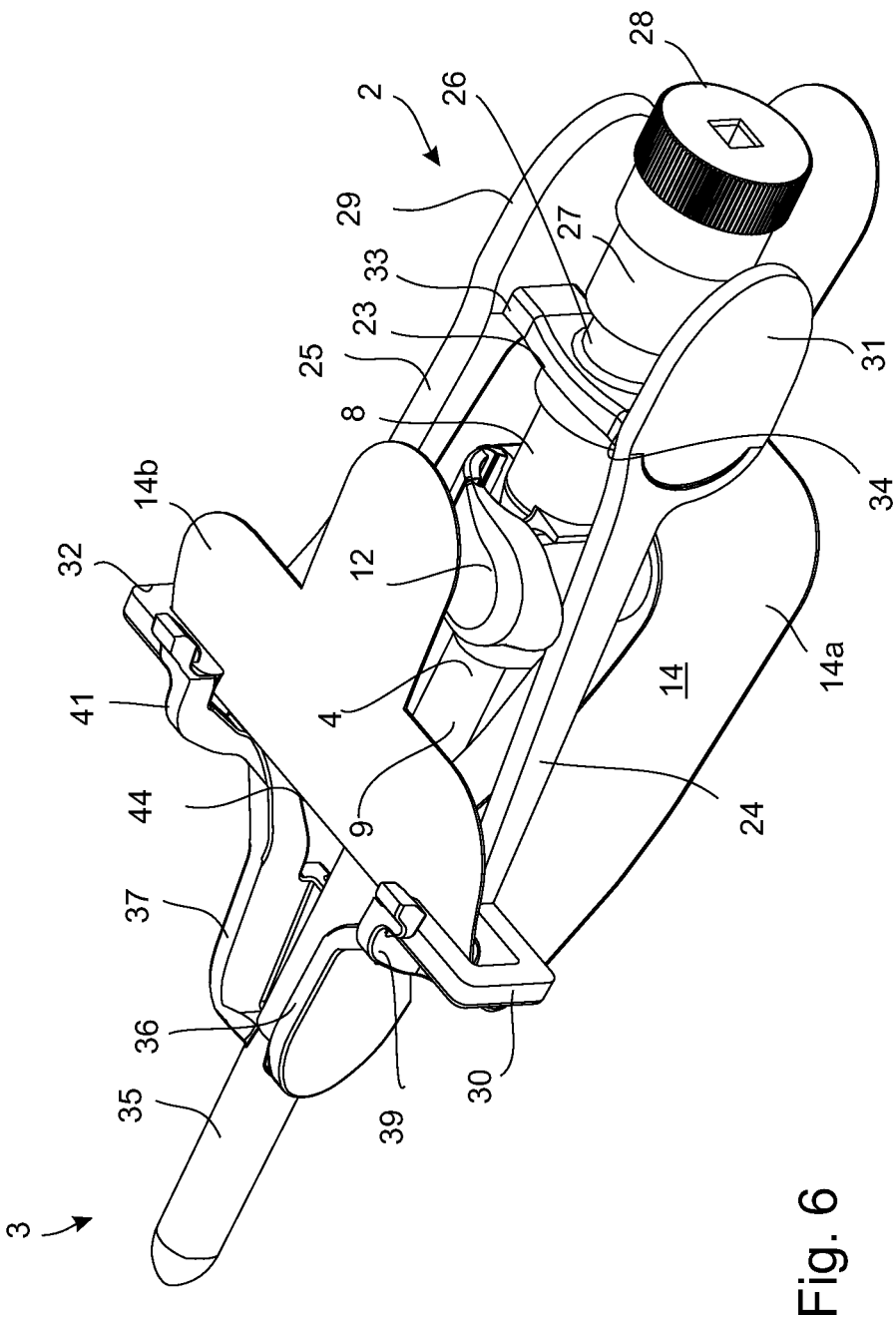
FIG. 6 shows, seen in perspective, the peripheral catheter and the inserter assembly in the assembled state.

FIG. 6 shows the peripheral catheter assembly mounted with the first inserter part 2 and the second inserter part 3. The needle 6 and the over-the-needle tube 5 extend through the plaster member 14 thereby arranging a proximal flap 14a below the needle hub 4 and a distal flap 14b above the needle 6 and the over-the-needle tube 5 so that said distal flap 14b can be folded back and located in the opposing openings of the U-bendings 30,32 or the hooks. The needle cover part 35 of the first inserter part 3 is arranged to cover the pointed tip 46 of the needle 6 to protect both an operator prior to use and the assembly itself to damages. The flexible first claw 39 of the first clamping arm 36 clamps around the U-bending 30 of the first leg 24 and traps distal flap 14b in a back-folded and non-displaceable manner. The flexible second claw 41 of the second clamping arm 37 clamps around the U-bending 32 of the second leg 25 and traps distal flap 14b in a similar back-folded and non-displaceable manner thereby defining a folding line 44. Although not visible in FIG. 6, it is emphasised that the valve sealing 7 is secured inside the needle hub 4 at the proximal female end 8 by means of the locking ring 19, and the proximal end 8 of the needle hub 4 is subsequently mounted, e.g force fitted, on the male socket 22 of the bridge member 23. At the opposite distal end 9 of the needle hub 4 the connection piece 20 serves for holding the needle 6 and catheter tube 5 secured to the needle hub 4. The female plug 26 is closed by a Luer connector 27, which again is end-capped by means of a plug 28. The Luer connector 27 has a bore extending through a male socket 27a fitting sealingly inside the proximal female end 8 of the catheter hub 4, and an opposing female end 27b for mating with e.g. the plug 28 or a male connector of a drip.

The insertion procedure will now be described step by step with reference to FIGS. 7-14.

Figure 7:
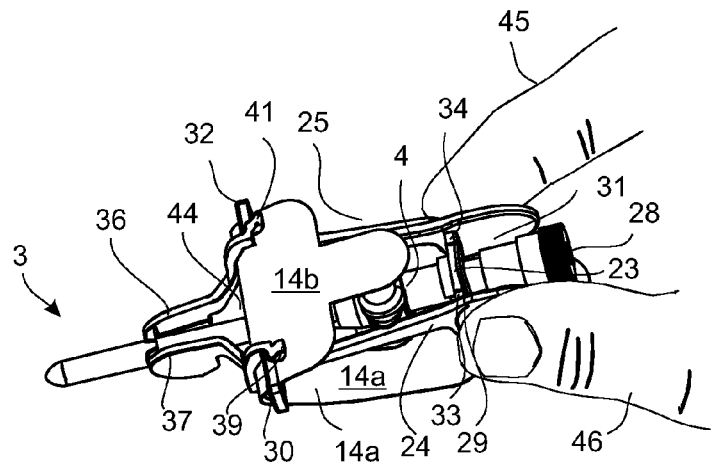
FIGS. 7-15 show a series of steps of performing a venipuncture using the inserter assembly according to the present invention for inserting an over-the-needle tube of a peripheral catheter assembly with an integral plaster member.
Figure 8:
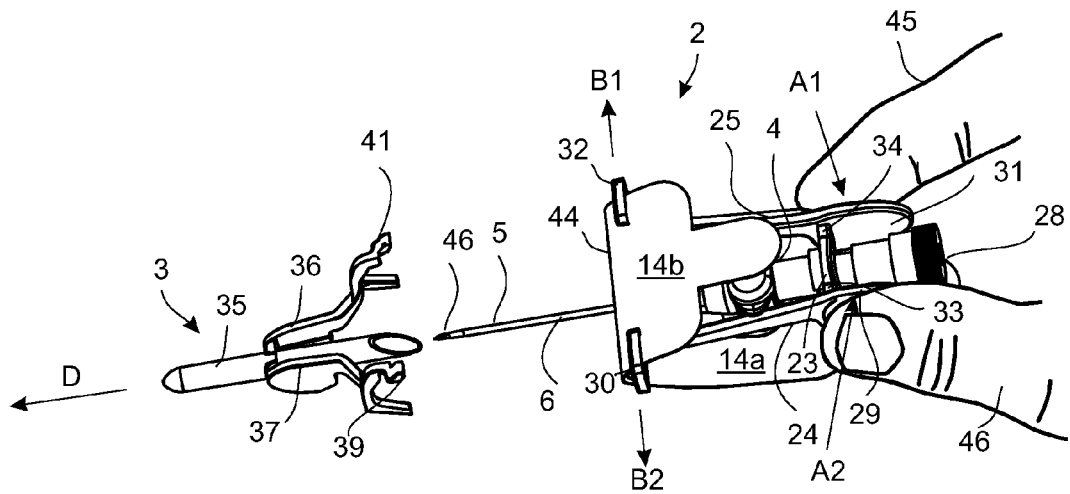

FIG. 7 corresponds to FIG. 6 but the opposing flat finger grip plates 29,31 are seen grasped between the index finger 45 and the thumb 46. Next, the opposing flat finger grip plates 29,31 are manually forced against each other using the fingers 44,45 to apply force as indicated by the arrows A1,A2 in FIG. 8. As a result of the application of force the distal ends 24b,25b, i.e. the U-bendings 30,32, of the respective first leg 24 and the second leg 25, flex about pivots 33,34 of bridge member 23 and are spread apart, resulting in that the first claw 39 and the second claw 41 disengage the coupling with the respective U-bendings 30,31 due to loosing contact with each other. After disengagement the second inserter part 3 can easily be removed from the first inserter part 2 and discarded, as indicated with the arrow D, exposing the pointed needle tip 46 of the needle 6 and holding the distal flap 14b of the plaster member 14 back-folded thereby configuring the peripheral catheter assembly 1 and the first inserter part 2 ready for use to insert the catheter tube 5 into e.g. a vein of a patients arm as will be described with reference to the subsequent figures.

Figure 9:
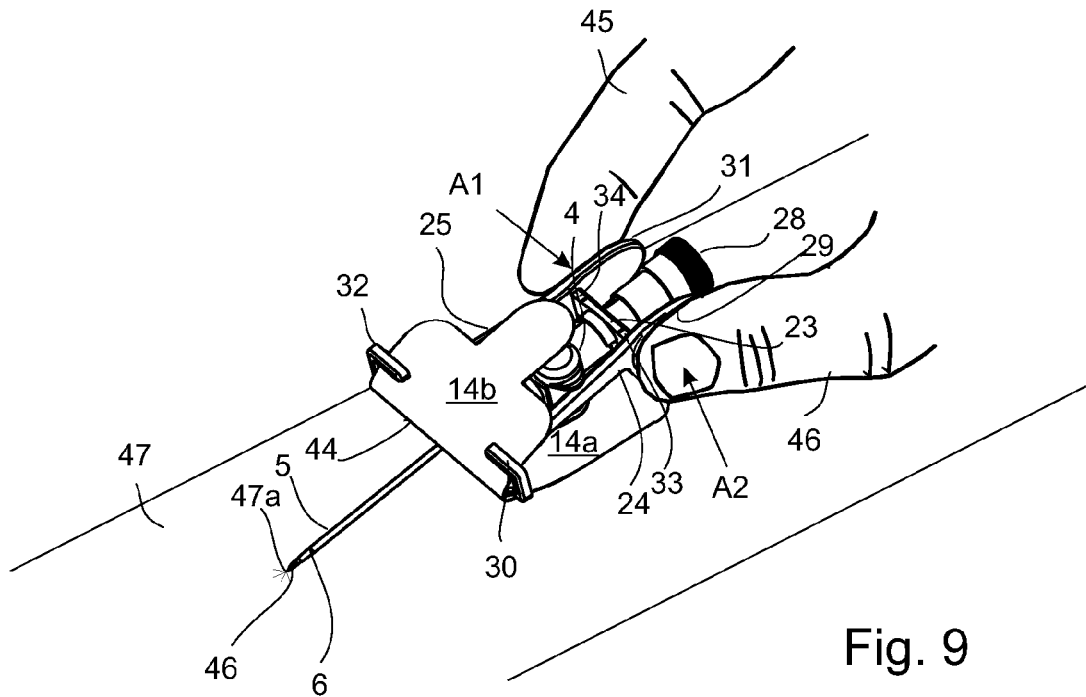

As shown in FIG. 9 the peripheral catheter assembly 1 and the first inserter part 2 is situated above a suitable site on a skin surface 47 for inserting the catheter tube 5 into a vein at a puncture site 47a. The first inserter part 1 is held by the fingers 45,46 in a manner already described for FIG. 8. Due to the enlarged gripping areas of the plates 29,31 the fingers 45,46 can be used for both pivoting the legs 24,25 and for controlling the needle insertion process in the direction F, as seen in FIG. 10, to a higher degree than insertion of known peripheral catheter needles, while the first leg 24 and second leg 25 at the same time serve for holding the distal end 14b of the plaster member 14 away from the puncture site 47a, thereby providing a free line of view and reducing the risk of off-target puncture and hematomas.

Figure 10:
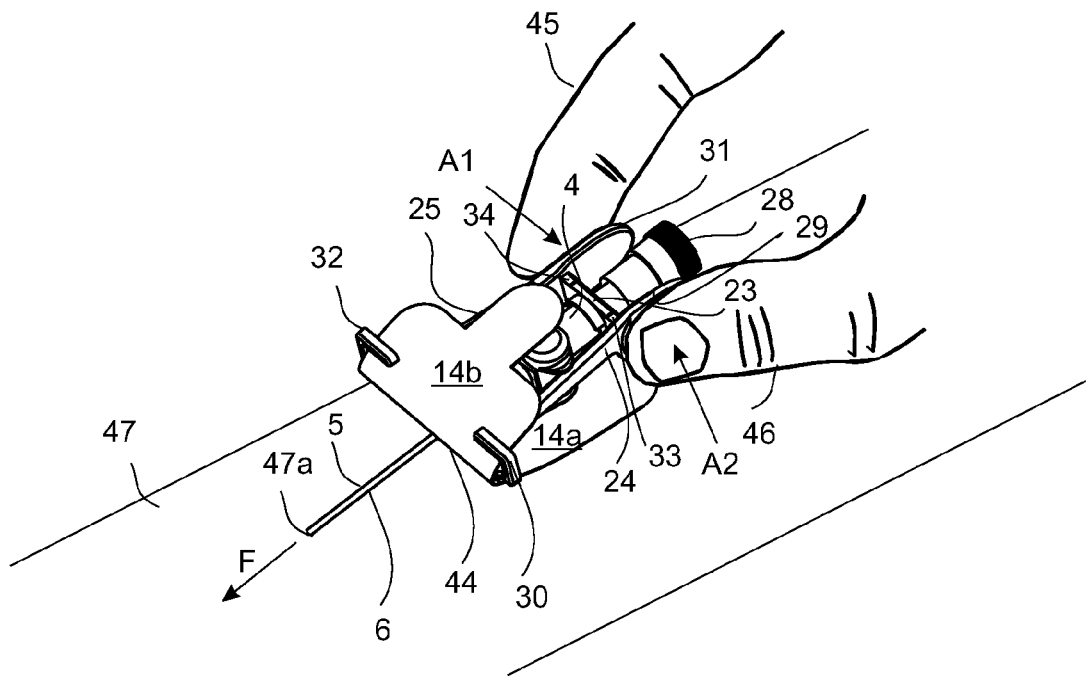
Figure 11:
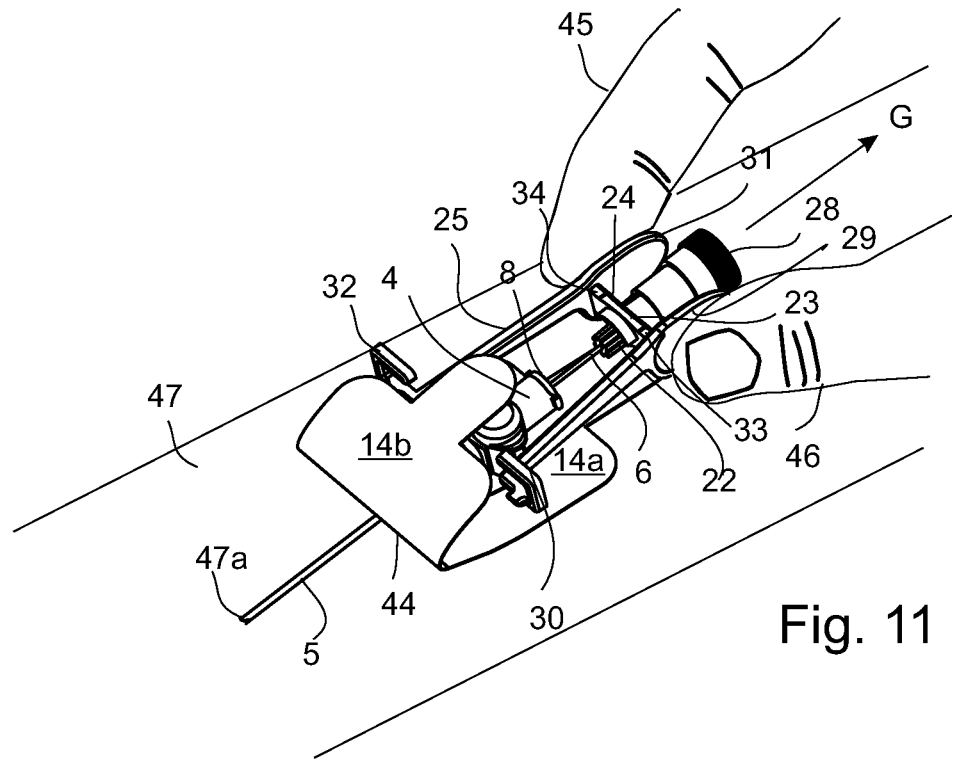
Figure 12:
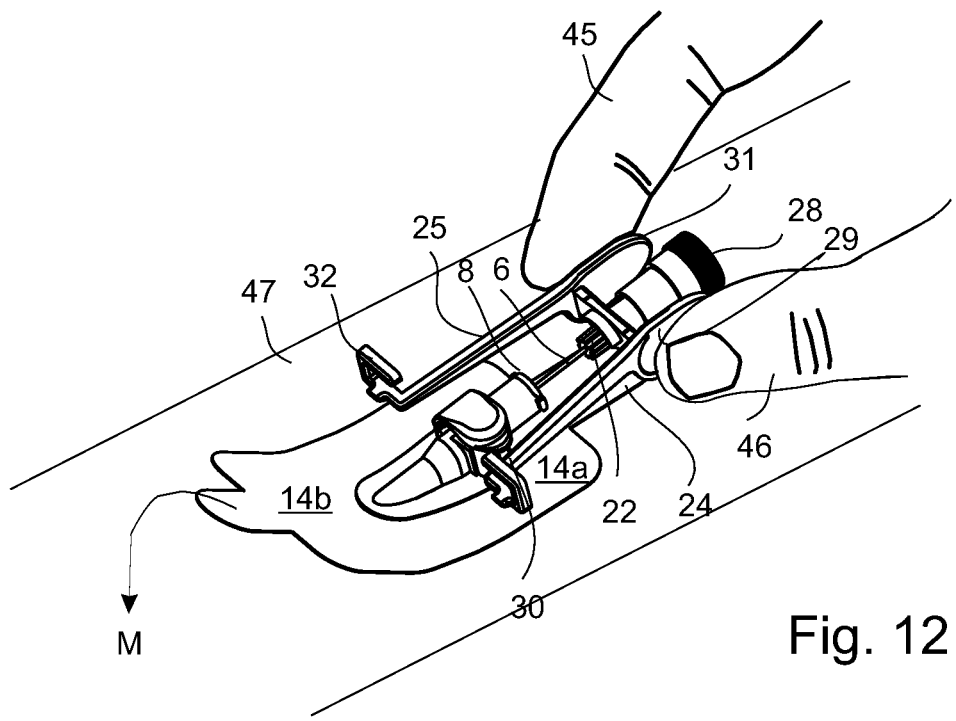
Figure 13:
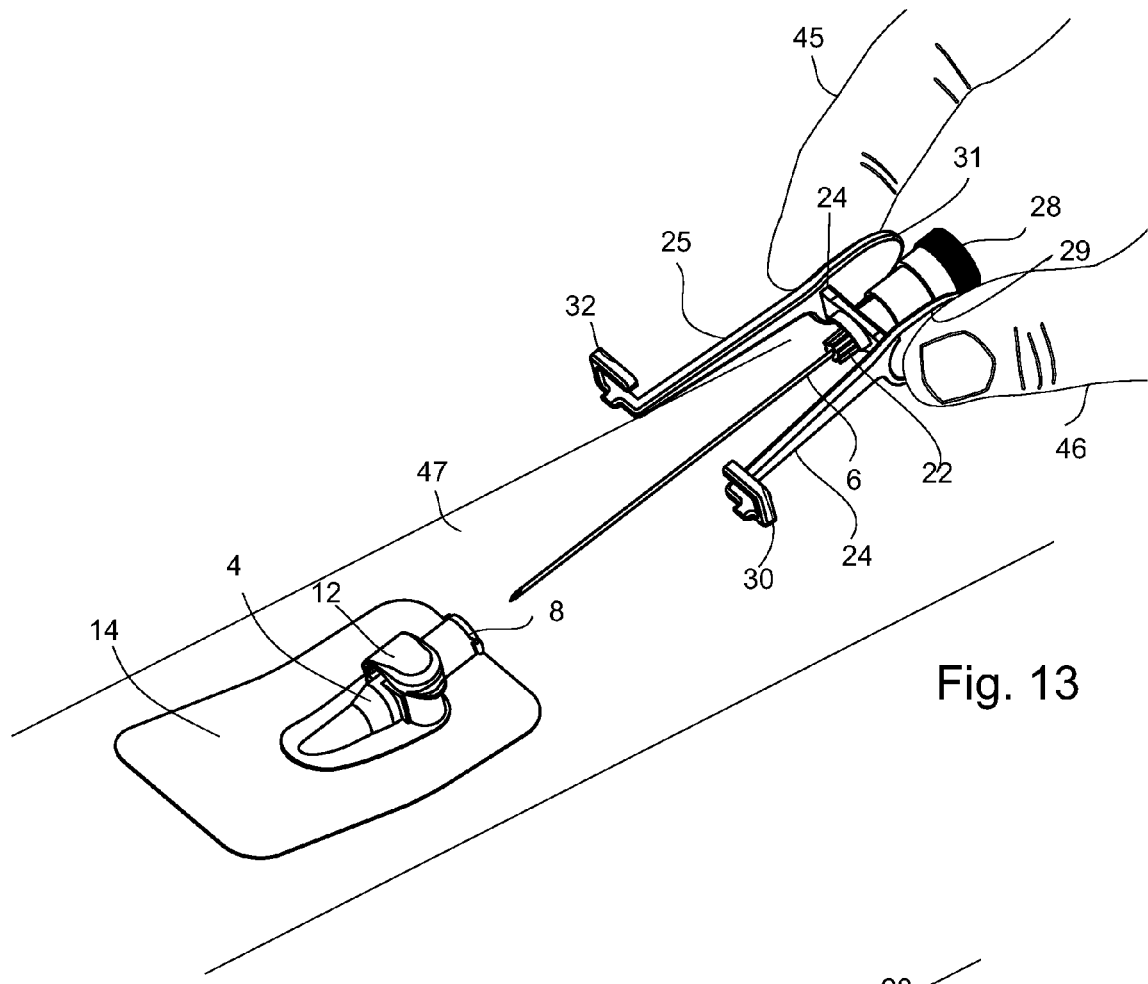

When the needle is correctly positioned inside the vein as seen in FIG. 10, the needle holding male socket 22 of the bridge member 23 of the first inserter part 2 is disengaged from the proximal end 8 of the catheter hub 4 by pulling the first inserted part 2 and the needle 6, which is secured in the male socket 22 of the bridge member 23 and in this case forms part of the needle module, in the direction G as seen in FIG. 11, to retract the needle 6 from the catheter tube 5, which is left inside the vein, for providing an administration line to the blood vessel. As seen in FIG. 12 the distal end 14b of the plaster member 14 is thereby set free and swings back as indicated by the arrow M so that the plaster member can be adhered to the subjacent skin surface 47, as is seen in FIG. 13, once the releasable cover sheet 16 has been removed.

Figure 14:
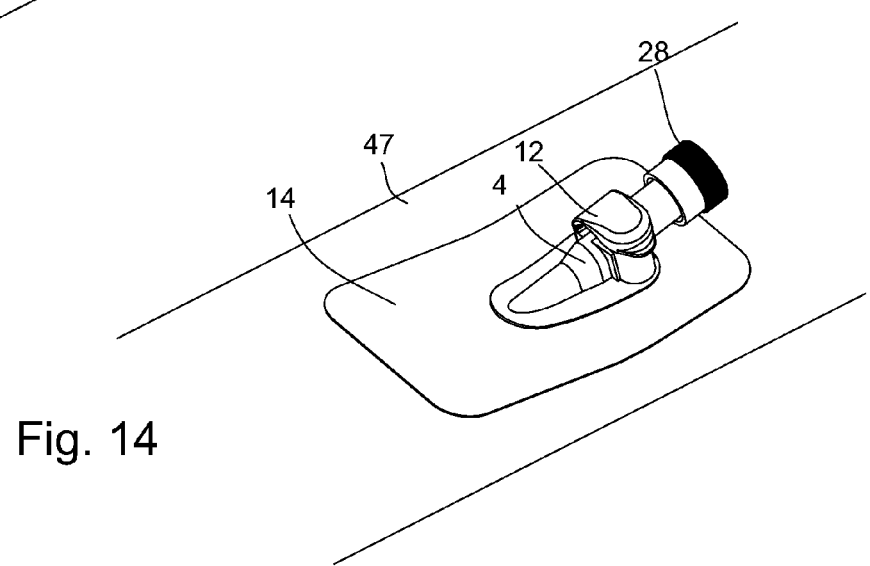

As illustrated in FIG. 14 the closure plug 28 can be used as a temporary closure of the proximal end 8 of the needle hub 4 if desired, but in the alternative the sealing valve serves as a non-return valve that prevents blood spillage and provide the operator with a high degree of freedom to manipulate as described in the applicants own international patent application no. PCT/EP2008/059950.

Figure 15:
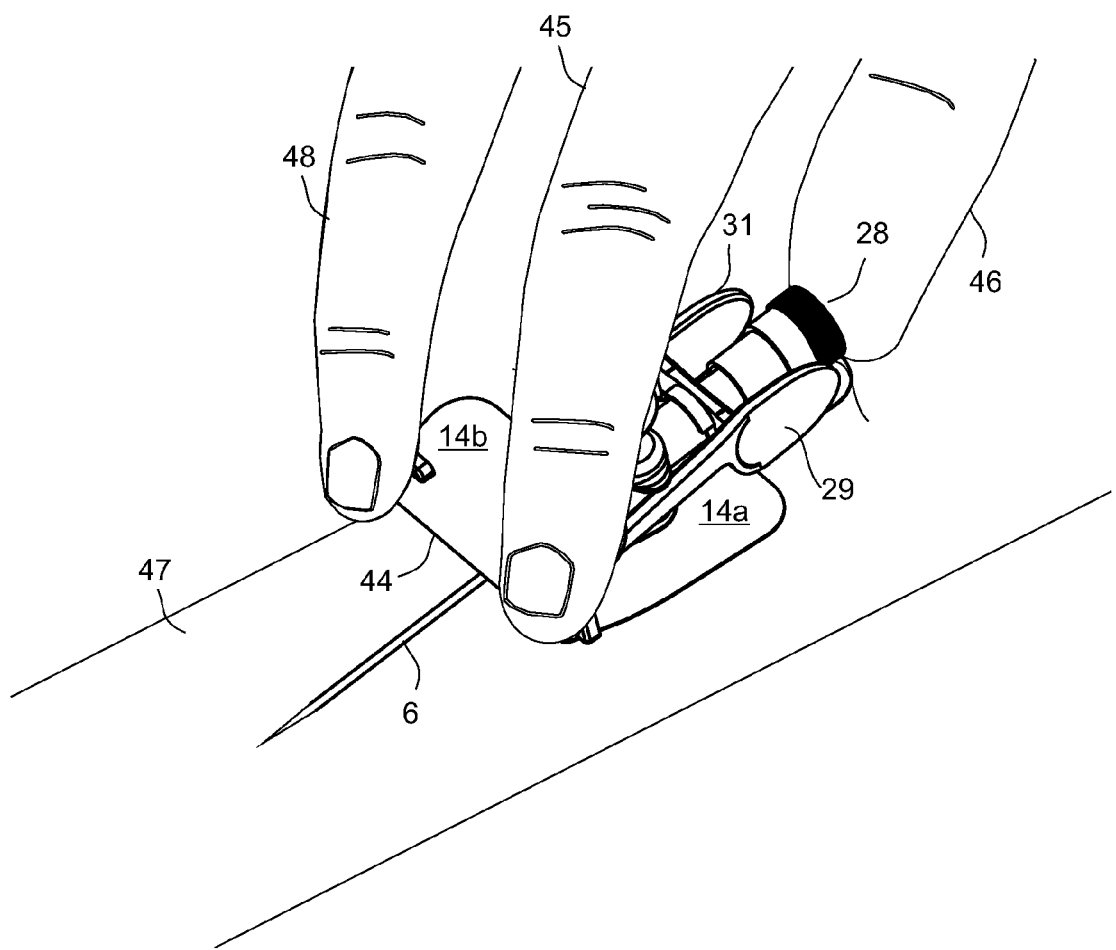

FIG. 15 shows an alternative way of inserting the catheter tube 5 into a patient's vein using the inventive inserter assembly 2,3 according to the present invention for controlled view to the puncture site 47a and for guiding the peripheral catheter assembly 1. In this case no pressure is applied to the finger grip plates 29,31, as this is not required. Instead the thumb 46 is used for abutting the plug 28 and applying a forward insertion force. The index finger 45 rests on the U-bending 30 of the first leg 24 and the third finger 48 rests on the U-bending 32 of the second leg 25.

The positions of the fingers during venipuncture can be made just as preferred by the operator.

The blood vessel puncture is made under conditions as close to aseptic as conceivable possible. Moreover the stable guiding and hold of the needle by means of the first inserter part reduces the risk of accidental penetration of the blood vessel wall. The risk of losing the grip at the combined peripheral catheter and inserter assembly is substantially smaller than the risk of loosing the grip on e.g. the wings of a conventional peripheral catheter. Once the peripheral catheter assembly has been properly inserted in a smooth insertion procedure properly assisted, guided and hold by the inserter assembly the adhesive surface of the plaster member is adhered to the patient around the puncture site to prevent access of contaminants. The adhering plaster member ensures that the peripheral catheter is not unintentionally dislocated, and the smooth and fast insertion procedure for the catheter tube reduces the risk of causing irritation, phlebitis and embolism subsequent to insertion.

The scope of the invention is not limited to the foregoing specification, but instead is given by the appended claims along with their full range of equivalents.

What is claimed is:

1. An inserter assembly for a peripheral vein catheter assembly comprising:
   a hollow catheter hub having a female proximal end and a distal end provided with a catheter tube;
   a needle module having a male coupling part for engaging the female proximal end of the hollow catheter hub and provided with a needle extending inside the catheter tube and having an axis and pointed tip protruding from the catheter tube;
   a plaster member secured to the needle module and having a first adhesive surface and an opposing second surface, wherein the catheter tube extends through the plaster member from the first surface to the second surface and the plaster member is configured for folding crosswise the needle axis along the longitudinal axis or length of the needle;

wherein the inserter assembly comprises:
a first inserter part having first and second legs;
a bridge member connecting the first and second legs at a distance from each other, with the bridge member adapted for detachably engaging or holding at least a part of the needle module extending coaxially between the first and second legs,
wherein the first and second legs are provided with holding means adapted for detachably holding a back-folded part of the plaster member.

2. The inserter assembly according to claim 1, wherein the means for detachably holding a back-folded part of the plaster member is a hook or a U-bend extension provided at the distal end of respective first and second legs.

3. The inserter assembly according to claim 2, wherein the proximal ends of the first and second legs have enlarged finger grip sections.

4. The inserter assembly according to claim 1, wherein the first and second legs have respective proximal ends and opposing distal ends, and the bridge member connects the legs at a distance from the respective proximal ends at respective connection points on the legs and the plaster member is secured to needle module.

5. The inserter assembly according to claim 4, wherein the distance between the proximal end of a leg and its corresponding connection to the bridge member is shorter than the distance between the connection and the distal end of the leg.

6. The inserter assembly according to claim 1, further comprising a first pivot to provide the connection between the first leg and a first end of the bridge member and a second pivot to provide the connection between the second leg and the second end of the bridge member opposite the first end.

7. The inserter assembly according to claim 1, wherein the first and second legs are pivotable to and from each other along the length of the needle module.

8. The inserter assembly according to claim 1, wherein the inserter assembly further comprises a second inserter part including a needle cover part.

9. The inserter assembly according to claim 8, wherein the second inserter part has first and second clamping arms attached to the needle cover part, with the first and second clamping arms adapted for detachably coupling with the holding means of the first inserter part for detachably holding a back-folded part of the plaster member.

10. The inserter assembly according to claim 9, wherein the first clamping arm has a free end provided with a first clamp means and the second clamping arm has a free end provided with a second clamp means, with the first and second clamp means designed for detachably coupling with the holding means of the first inserter part for detachably holding a back-folded part of the plaster member.

11. The inserter assembly according to claim 9, wherein the first and second clamping arms are resiliently arranged on the needle cover part.

12. The combination of a peripheral vein catheter and the inserter assembly recited in claim 1.

13. An inserter assembly for a peripheral vein catheter assembly comprising:
a hollow catheter hub having a female proximal end and a distal end provided with a catheter tube;
a needle module having a male coupling part for engaging the female proximal end of the hollow catheter hub and provided with a needle extending inside the catheter tube and having an axis and pointed tip protruding from the catheter tube;
a plaster member secured to the needle module and having a first adhesive surface and an opposing second surface,
wherein the catheter tube extends through the plaster member from the first surface to the second surface and the plaster member is configured for folding crosswise the needle axis along the longitudinal axis or length of the needle module;
wherein the inserter assembly comprises:
a first inserter part having a first and second legs;
a bridge member connecting the first and second legs at a distance from each other, with the bridge member adapted for detachably engaging or holding at least a part of the needle module extending coaxially between the first and second legs,
wherein the distal ends of the first and second legs are provided with a hook or extension adapted for detachably holding a back-folded part of the plaster member.

14. The combination of a peripheral vein catheter and the inserter assembly recited in claim 13.

15. A method for configuring a peripheral vein catheter assembly with an inserter assembly according to claim 13, which comprises:
mounting the needle module in or at the bridge member of the first inserter part;
folding the plaster member perpendicularly and back towards the proximal ends of the first and second legs of the first inserter part;
mounting the second inserter part to cover the needle of the needle module; and
detachably coupling the first inserter part to a second inserter part.

16. A method for performing a blood vessel puncture which comprises:
configuring a peripheral vein catheter assembly with an inserter assembly according to claim 15,
detaching the second inserted part;
inserting the catheter tube into a blood vessel at a puncture site;
retracting the needle by retracting the first inserter part, thereby leaving the catheter tube inside the blood vessel and setting the plaster member free; and
adhering the plaster member to a skin surface around the puncture site.

17. The method of claim 16 which further comprises pressing the first and second legs of the first inserter part together towards the needle module prior to inserting the catheter tube.

18. A method for configuring a peripheral vein catheter assembly with an inserter assembly according to claim 8, which comprises:
mounting the needle module in or at the bridge member of the first inserter part;
folding the plaster member perpendicularly and back towards the proximal ends of the first and second legs of the first inserter part;
mounting the second inserter part to cover the needle of the needle module; and
detachably coupling the first inserter part and the second inserter part together.

19. A method for performing a blood vessel puncture which comprises:
configuring a peripheral vein catheter assembly with an inserter assembly according to claim 18;
detaching the second inserted part;
inserting the catheter tube into a blood vessel at a puncture site;
retracting the needle by retracting the first inserter part, thereby leaving the catheter tube inside the blood vessel and setting the plaster member free; and adhering the plaster member to a skin surface around the puncture site.

20. The method of claim 19 which further comprises pressing the first and second legs of the first inserter part together towards the needle module prior to inserting the catheter tube.

\* \* \* \* \*